United States Patent
Wiktor et al.

(10) Patent No.: US 10,183,103 B2
(45) Date of Patent: Jan. 22, 2019

(54) CASSETTE MODULE HAVING AN INTEGRATED CENTRIFUGAL PUMP UNIT

(71) Applicant: Fresenius Medical Care Deutschland GmbH, Bad Homburg (DE)

(72) Inventors: Christoph Wiktor, Gelnhausen (DE); Alexander Heide, Eppstein (DE); Manfred Weis, St. Wendel (DE); Goekhan Oerter, Weilmuenster (DE); Marina Wenke, St. Wendel (DE); Udo Waeber, Offenbach (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 431 days.

(21) Appl. No.: 14/787,114

(22) PCT Filed: Apr. 16, 2014

(86) PCT No.: PCT/EP2014/057683
§ 371 (c)(1),
(2) Date: Oct. 26, 2015

(87) PCT Pub. No.: WO2014/173744
PCT Pub. Date: Oct. 30, 2014

(65) Prior Publication Data
US 2016/0067394 A1 Mar. 10, 2016

(30) Foreign Application Priority Data

Apr. 25, 2013 (DE) .................. 10 2013 007 190

(51) Int. Cl.
*A61M 1/10* (2006.01)
*A61M 1/14* (2006.01)
*F04D 1/00* (2006.01)

(52) U.S. Cl.
CPC .............. *A61M 1/101* (2013.01); *A61M 1/14* (2013.01); *F04D 1/00* (2013.01); *A61M 1/1006* (2014.02);
(Continued)

(58) Field of Classification Search
CPC .. A61M 1/1006; A61M 1/101; A61M 1/1031; A61M 1/14; A61M 2205/12; F04D 1/00
See application file for complete search history.

(56) References Cited

U.S. PATENT DOCUMENTS 8,979,798 B2 3/2015 Shener et al.

FOREIGN PATENT DOCUMENTS

DE 3923692 1/1991
DE 102009018664 10/2010
(Continued)

*Primary Examiner* — John Kim
(74) *Attorney, Agent, or Firm* — Jacobson Holman, PLLC.

(57) ABSTRACT

The invention relates to a cassette module for processing blood and therapeutic fluids in an extracorporeal blood treatment, dialysis or infusion technology, comprising a base body (302), with a first side and a second side, fluid channels integrated into the base body, a receiving unit (304) to receive a centrifugal pump means for delivering fluids, characterized in that at least some of the fluid channels are arranged on a first side of the base body, and the receiving unit for the centrifugal pump means is arranged on the second side, and the receiving unit for the centrifugal pump means is in fluid connection with the fluid channels on the first side during operation.

12 Claims, 4 Drawing Sheets

① Machine plate
② Pump drive
③ Position pin
④ Disposable with integrated rotor and position bore

(52) U.S. Cl.
CPC ....... *A61M 1/1031* (2014.02); *A61M 2205/12* (2013.01)

(56) References Cited

FOREIGN PATENT DOCUMENTS

| | | |
|---|---|---|
| DE | 102009058681 | 6/2011 |
| EP | 1909864 | 4/2008 |
| EP | 1930034 | 6/2008 |
| WO | WO 95/23627 | 9/1995 |
| WO | WO 2006/120415 | 11/2006 |
| WO | WO 2011/020600 | 2/2011 |

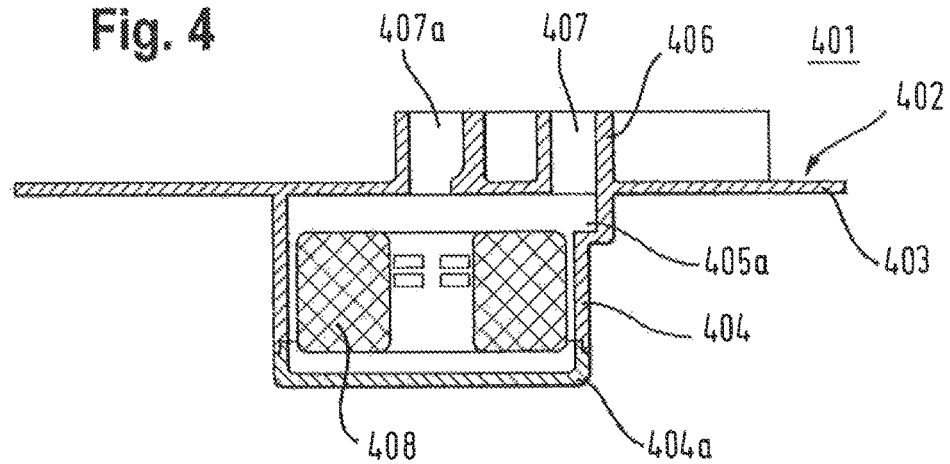
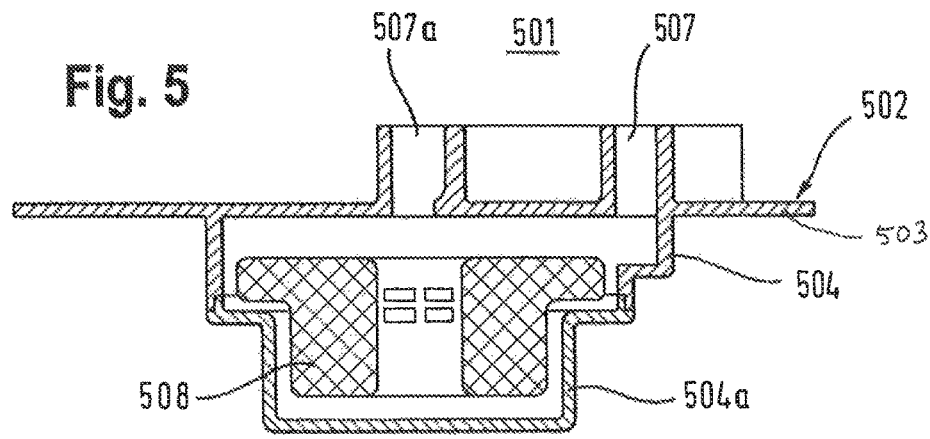
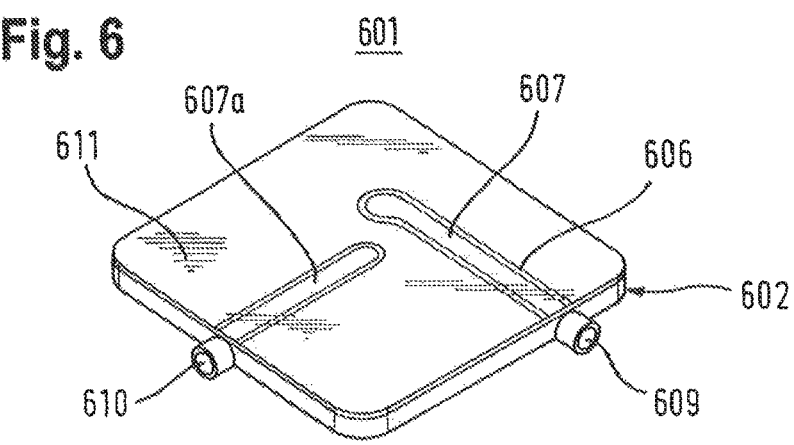

① Machine plate

② Pump drive

③ Position pin

④ Disposable with integrated rotor and position bore

CASSETTE MODULE HAVING AN INTEGRATED CENTRIFUGAL PUMP UNIT

The subject matter of the invention relates to the field of integrated cassette modules for use in therapeutic methods of extracorporeal blood treatment, peritoneal dialysis or infusion.

The invention relates in particular to therapeutic treatments in dialysis. In the case of an extracorporeal blood treatment by hemodialysis, toxic constituents of blood are separated via an extracorporeal blood circulation on a synthetic membrane of a dialysis filter.

The invention also relates to hemofiltration and hemodiafiltration, whose treatment methods are used with the methods of hemodialysis. The present invention is equally applicable for methods of hemofiltration and hemodiafiltration. Therefore, for further discussion, the term "hemodialysis" should also be understood to include hemofiltration and hemodiafiltration methods.

The present invention also relates to peritoneal dialysis. In peritoneal dialysis, a patient's peritoneum is filled with a dialysis fluid, and toxic metabolites are introduced through the membrane of the abdomen into the peritoneum. Then the dialysis fluid is discharged from the peritoneum.

The present invention also relates to blood treatments in transfusion, in particular in cell separation. Cell separation involves separating blood into its components in a centrifugation processing step in a blood centrifuge.

The present invention also relates to the fields of infusion, in which treatment fluids are infused into the patient.

Administration of fluids to a patient in the aforementioned treatments must be monitored from a medical standpoint and must proceed with safety precautions. Important tasks in fluid processing of fluids to be administered consist of thermal regulation of fluids, degassing and gas separation, balancing of the fluids removed with the fluids administered, monitoring the delivery of the fluid removed and that administered, filtration as well as the analysis of the fluids conveyed.

For a further standardization of terminology, process steps of the aforementioned type of treatment-relevant fluids in extracorporeal blood treatment, peritoneal dialysis or infusion in conjunction with the present description of the invention are referred to as fluid processing.

Cassette modules are used in the aforementioned therapeutic methods to process treatment-relevant fluids, which are administered to a patient in this sense.

The goal in the present development of cassette modules is to increasingly integrate more and more functions of fluid processing into cassette systems.

In the therapeutic procedures of the aforementioned type, which are customary at the present time, a cassette module is operated by a machine unit of a treatment machine, which triggers the function units on the cassette for fluid processing in a targeted manner. The required processing steps of fluids of a therapeutic method are performed partially or preferably entirely on the cassette module. This offers the advantage that treatment-relevant fluids do not come in contact with parts of the treatment machine, as is customary in the alternative. If the cassette modules are designed as disposable articles, they can be discarded after a treatment. Corresponding disinfection steps may be eliminated with the single use of the cassettes, so that no additional disinfection equipment is needed. The machine side thus has a less complex structural design. A high degree of integration of function units on a cassette also ensures significant savings of material due to the compact design.

Cassette modules are usually constructed of several components to form a cassette module. As a rule, a cassette module is produced from one or more flexurally rigid base bodies. Films and lengths of tubing are used as additional components. The components are preferably made of plastic materials, so this offers the possibility of manufacturing the cassette modules economically by mass production methods. Inexpensive extrusion and injection molding methods in particular are used for the manufacturing the cassette modules. One essential requirement in the development and production of cassette modules is the possibility of manufacturing a cassette module in the fewest possible simple process steps. This idea is ultimately associated with efforts to minimize manufacturing costs in production of the cassette modules.

Cassette modules are in particular also produced using integrated pump means. Known cassette modules have tubing segments, which deliver fluid through the cassette and the patient's lengths of tubing through a type of peristaltic action by means of a pump actuator, for example, the rotor of a rotary pump or the rams of a finger pump.

An alternative pump mechanism for extracorporeal blood treatment and infusion treatments is provided by centrifugal pumps on cassette modules. The centrifugal pumps also include the pumps known as impeller pumps, among others. These pumps have a rotor as the centrifugal pump means accommodated in a surrounding housing. Fluids are pumped through the housing in that the rotor is set in rotation. Such pumps are often used in cardio technology and in the oxygenation of blood. The rotors may be supported magnetically in a non-contact process by a surrounding external magnetic field in the pump housings using as the pump actuator only one unit, which creates a magnetic field for driving the rotor on one side of the machine. If pumping means and the pump actuator are brought into magnetic engagement, control of the actuator may be eliminated.

STATE OF THE ART

DE 39 23 692 A1 describes a blood treatment unit for oxygenation of blood. A rotor which conveys blood through the treatment unit is integrated into the treatment unit.

WO 95/23627 A1 discloses a cassette for conveying wound rinsing fluid. A rotor for conveying rinsing fluid is arranged between two plate parts of the cassette. The rotor is operated mechanically by means of a shaft, which is connected to a drive motor.

EP 1 909 864 A1 discloses a cassette system, in which a rotor of an impeller pump is arranged between two cassette plates. The rotor is supported purely magnetically and can be driven by an external magnetic field, which is provided by a control unit.

Starting from the relevant state of the art, so far there is no known embodiment of a cassette module having a base body, which has prepared structures to receive centrifugal pump means and to guide fluid streams and in which the structures are arranged and constructed, so that they can be manufactured together with the base body in a simple injection molding operation.

DESCRIPTION OF THE INVENTION

One problem with the construction and production of a base body of a cassette module having a receiving unit for a centrifugal pump means and integrated fluid channels through a simple injection molding process step is derived from the design and the flow characteristics of centrifugal pumps. The fluid must flow axially into the pump housing, namely along the axis of rotation of the rotor. However, an outflow of fluid accelerated by the rotor must be tangential to the rotating rotor in order to be able to utilize the maximum flow energy of the fluid.

This requires the inflow and outflow of fluids into and out of the pump housing at different levels. For the integration of a centrifugal pump unit into a cassette module, the problem then arises of arranging the centrifugal pump unit on the base body of the cassette module, so that the inflow and outflow ports at different levels can be optimally connected to the fluid channels integrated into the base body. The problem consisted in particular of finding a geometry for an injection-molded part of a cassette module base body that would meet the requirements stipulated above and could be manufactured by a simple one-step process by injection molding.

According to the invention, this object is achieved by a cassette module having the features of Claim 1.

In addition, there was the need to find a possibility with which a cassette module having fluid channels and a receiving unit for a centrifugal pump means could be brought reliably into engagement with a machine console provided for operation of the cassette module, so that reliable actuation could be ensured on the machine side and liquid processing on the cassette module can be ensured.

This object is achieved by an arrangement consisting of a cassette module and a machine console according to the features of Claim 14.

Another object of the invention was to discover a simple injection molding method by means of which a base body of a cassette module could be produced and which would include a receiving unit for a centrifugal pump means and would have fluid channels which establish a fluid connection with the receiving unit.

The cassette module according to the invention is thus based on a base body, which has a first side and a second side. Fluid channels, which are provided for conducting blood or other treatment fluids to various function devices on the cassette module, are integrated into the base body. The fluid channels may be integrated into a first side of the cassette module or they may be integrated into a first side and a second side of the cassette module. In addition, the base body comprises a receiving unit for a centrifugal pump means. In particular, fluids such as blood or treatment fluids, e.g., dialysis fluids, are conveyed through the cassette by the operation of the centrifugal pump means. In preferred embodiments, the receiving unit is an integral component of the base body.

The base body forms a part of a cassette module. It may in particular be connected to other components to supply a ready-to-use cassette module. It has proven successful to manufacture cassette modules in a flat design, so that optimal engagement of the cassette module and the dialysis machine can be achieved in this way.

Accordingly, a base body may be a flat structure whose side lengths are many times greater than the height of the base body. In this analysis, the base body has a first side, which may be a top side when the base body is placed on its side having the long side lengths with respect to the height. A second side may be a lower side face in this depiction.

Integrated fluid channels are arranged on a first side, for example, the top side, or on a first side and a second side of the base body. The term "integrated" as used here is understood to mean that the channels and the base body are manufactured in one piece. The receiving unit for a centrifugal pump means is arranged on a second side, e.g., on the bottom side of the base body in the depiction described here.

In addition to the purely magnetic support of the rotor, it is also possible for the support to be provided through fluidic and magnetic means or for the support to be accomplished in part by a mechanical support. With regard to gentle delivery of sensitive liquids such as blood, it is provided that the rotor is supported purely magnetically. Fluidic support may be provided secondarily during operation of the rotor, but it is not effective for support when the rotor is at a standstill.

The receiving unit extends at least partially around the rotor and together with it forms a pump unit. Additional components may optionally be connected to the receiving unit and may completely surround the rotor, thus forming a pump chamber which has fluid flowing through it during operation. The receiving unit is preferably a pipe segment or a pipe end, which is adapted in the radius, so that it at least partially surrounds the centrifugal pump means, e.g., the rotor of an impeller pump.

The arrangement of fluid channels and the receiving unit in the fluid-connecting design on opposite sides of the base body permits a one-piece production of the base body by the injection molding method.

It has also proven to be advantageous that fluid channels and the pump unit can be manufactured very compactly on the cassette module. The delivery paths that must be traveled by the blood or the treatment fluids are minimized, so that damage to the fluids, e.g., due to hemolysis or contamination by the cassette material can be minimized.

The possibility of manufacturing the base body in one piece by the injection molding method eliminates seams and contact points of multicomponent manufacturing. This improves the compatibility of the cassette with the fluids to be processed, e.g., blood or other treatment fluids. A cassette module having a base body manufactured as described above is therefore especially suitable for use in hemodialysis or peritoneal dialysis.

In one embodiment, the base body of the cassette module may advantageously be refined, so that fluid channels on a first side of the base body form inlet and outlet lines for fluid streams to and from the receiving unit of the pump rotor. In this case, the base body has continuous passages through which the flowing fluid can be transferred from a first side on which the fluid channels are arranged to a second side on which the pump unit with the centrifugal pump means is located. A first through-port is advantageously arranged so that the inflowing fluid strikes the rotor in the axial direction. A second through-port is arranged so that the fluid emerging tangentially at the receiving unit of the centrifugal pump means is directed to the first side.

During operation, the cassette module on the side where the pump unit, comprising the receiving unit and the pump rotor is located, is brought into engagement with the machine console. The pump unit is then preferably inserted into a recess in the machine console. In this arrangement, it is advantageous that the fluid-carrying channels are mounted on the second side.

In a preferred embodiment, fluid channels which are in a fluid-carrying connection to the pump unit on the second side are integrated into a first side of the base body. The fluid channels are preferably arranged on the first side on the side facing away from the machine console when the cassette module has been inserted ready-to-use into the treatment machine. A fluid connection of the tangential outlet of the pump unit on the second side of the base body and the outgoing fluid channel on the first side is made possible by means of a fluid ramp. The fluid ramp is an obliquely inclined channel section. The fluid ramp is a construction section which can be manufactured easily with the additional embodiment of the base body in a one-step injection-molding process.

In an alternative embodiment, the fluid ramp is omitted because the production of the injection-molding tools must be developed very precisely for such a geometry, as already described above. It is therefore also possible that the tangential outlet on the receiving unit for the rotary pump means is mounted on the second side of the base body. The tangential outlet on the second side may be connected to tubes for conducting the flowing liquid further. For example, additional fluid-carrying components, which may be connected separately to the cassette module, may be connected via the tubing. Such components may include, for example, dialysis filters, drip chambers, clot catchers, measurement interfaces. However, in this arrangement, the base body may also be manufactured in one piece by a one-step injection-molding process. In this case, fluid channels may also be arranged on the second side of the base body. In particular, the tangential outlet on the receiving unit is integrally connected to an outgoing fluid channel.

In individual cases, however, other designs in which the base body with fluid channels and the receiving unit for the centrifugal pump means are designed in two parts are also conceivable. It is important that the fluid channels are arranged on a first side of the base body and that there are passages in the base body which allow flowing liquid to pass on the other side of the base body. The receiving unit may be a part that is manufactured separately and is connected to the base body by an adhesive bond or a welded joint. Alternatively, the receiving unit may also be connected to the base body by a mechanical fastening means.

The base body may advantageously surround a base plate on which the integral components are arranged. The fluid channels are formed by perpendicular wall sections which are arranged perpendicularly on the base plate. Perpendicular in this context is not to be understood to be a strict geometric arrangement of the base plate in relation to the channel wall. A slight unmolding slope in the shape of the channel walls is necessary for the production of the base body by the injection-molding process, so that the injection-molded base body can be taken out of the injection mold. The base of the wall, which is directly adjacent to the base plate of the base body, may therefore be designed to have a wider cross section than the wall sections at a distance from the base plate. The wall may thus have a slightly conical or concave shape in cross section. The term "perpendicular" here is therefore also understood in this context to mean that only the main alignment of the plane of the wall is perpendicular to the main alignment of the base plate.

The vertical wall sections to be understood by this term form a lateral border for the fluid channels. The transition from the base plate to the perpendicular wall sections may be designed to be angular or rounded in order to improve compatibility with sensitive treatment-relevant fluids such as blood, for example. Essentially two wall sections are arranged parallel to one another with a distance between them to form a channel, so that during operation of the cassette, a fluid such a blood or a treatment fluid can flow between the wall sections and along the channel. To this end, the perpendicular wall sections must be covered, forming a closed channel by the combination of the base plate with the perpendicular wall sections and the cover. The wall sections in additional sections of the base body also need not run in parallel. In particular, the wall sections may also be part of a functional subunit on the base body, e.g., a clot catcher for blood clots or an air separation chamber, in which the wall sections no longer run in parallel.

The cover may be formed by a flexurally rigid sheet, but the cover is preferably formed by a flexible film. Use of the flexible film for constructing the cover has the advantage that tolerances in manufacturing the base body are easily compensated. The perpendicular wall sections are preferably designed so that all the wall sections have the same height. According to a welding method which is well known in the state of the art, the covering film or sheet may be pressed onto the base body over a pane of glass, for example, and may be welded along predetermined contours with point precision using a laser penetration welding method. The welding contours are predetermined in particular by the perpendicular wall sections, which are pressed against the film.

In some cases, some or all of the channels may be covered with film pieces, which correspond exactly to the size of the channel. However, from the standpoint of production technology, it is simpler to cover larger parts of the base body with a film and to weld it along the course of the wall sections of the fluid channels. The fluid channels may be covered in one welding operation in this way.

Like the wall sections of the fluid channels, the wall sections of the receiving unit for the centrifugal pump means may be formed by perpendicular wall sections which stand at a right angle on a base plate of the base body. The cross section of the receiving unit is essentially round in particular. However, it is also possible to deviate from the round shape if the preferred geometric shape must be disturbed by connections. On the whole, the receiving unit is a cylindrical shape, in which the liquid to be processed is accelerated by the rotor and flows through the outlet into the outgoing channel during operation of the pump unit.

The receiving unit may be designed to be more or less tall. This also depends on the geometry of the rotor. The receiving unit may be covered in conjunction with a corresponding round cap, so that the rotor is completely enclosed in the pump unit. The perpendicular wall sections of the receiving unit, the base plate, the cover with a cap, the inlet and outlet for fluids and the rotor together form the pump unit.

The cover may also be provided by a film to compensate better for manufacturing tolerances in the cassette base body by using a covering film.

The rotor drive itself is separate from the receiving unit of the rotor and is a component of a machine console. The machine console and cassette module are shaped, so that they have complementary surface profiles. Accordingly, the machine console has a surface profile into which the cassette module can be placed. A directly opposed arrangement of the suitably shaped surfaces of the machine console and the cassette module is necessary because interactions between the machine console and the cassette module may occur during operation of the unit. Such interactions occur, e.g., due to sensors which are accommodated in the machine console and are in interaction with the cassette module or with the liquids guided therein during operation of the cassette module, interacting mechanically, acoustically, thermally, inductively, optically, magnetoresistively or electrically, for example. For this reason and for sensor signal detection, it is necessary for the sensor units and the area of the cassette module that is to be analyzed to be in opposition geometrically.

Starting from a cassette module of the type described in the introduction, there has therefore still been the problem of finding an arrangement with which a cassette module can be inserted correctly into a corresponding console of a dialysis machine, so that the required interactions between the dialysis machine and the cassette module can proceed with proper function. This problem has been solved by mounting a molded part, which can be brought into engagement uniquely with a corresponding section having a complementary shape on the cassette module, on the machine console. "Uniquely" here should be understood to mean that there is only one position of the cassette and the machine console that can result in a form-fitting arrangement. The molded part may have a polygonal cross section, for example, a triangular, quadrilateral or pentagonal, oval, asymmetrical or circular shape.

However, despite the correct positioning in relation to the machine console, the cassette may assume a tilted or inclined position in relation to the machine console, so that not all sections of the cassette and the machine console can enter into a direct interaction.

To check on the correct arrangement, it is therefore also necessary for the position of the cassette and the machine console to have an additional connecting unit, which allows one to check on whether the cassette is completely in the correct arrangement in relation to the machine console. Within the context of the present invention, this connection is established by means of a magnet. A magnetic element is accommodated structurally in the cassette module. A corresponding magnetic counterpart is located in the machine console, so the cassette module is held on the machine console by magnetic attraction. The position of the cassette module in the arrangement with the machine console is already partially predetermined via the first molded part of the machine console and the engagement with the cassette module. The magnetic connection ensures that the cassette is positioned correctly and is not in a faulty tilted position on the machine console.

It is provided in particular that the magnetic element is accommodated on a first side of the cassette module, which faces the machine console. In another embodiment, the cassette module has a receiving unit for this purpose, in which the magnetic element of the cassette module is located. Alternatively, the magnetic element is a magnetic centrifugal pump means, i.e., in particular a magnetic rotor of an impeller pump. The magnetic drive on the machine console is designed, so that the receiving unit of the centrifugal pump means can be fitted into the magnetic drive. On the machine end, a modified magnetic field can be detected by a corresponding sensor system and processor unit when the receiving unit with the magnetic rotor is engaged with the impeller drive. It is thus possible to ascertain, by means of an analysis unit in the processor and by means of the recorded data on the altered magnetic field, whether the cassette is in a correct configuration with the machine console. This can be ensured only if the cassette is also engaged with the molded part of the machine console.

A cassette base body of the type according to Claim 1 as defined in the introduction can be manufactured by a one-step injection-molding process, which is explained in greater detail below.

According to the geometric arrangement of fluid channels, a receiving unit for the centrifugal pump means and the fluid ramp at the outlet channel of the receiving unit on the first side and on the second side of the base body, the base body may be manufactured in one piece by injection molding.

A corresponding injection-molding process comprises the steps of providing a mold, which has a profile that is complementary to the first side of the base body, where the first side of the base body is a side containing fluid channels. The fluid channels are formed here from perpendicular wall sections, as described in the introduction, these wall sections being arranged at right angles on a base plate of the base body.

The base plate of the base body itself has recesses which permit a fluid connection between the fluid channels on the first side of the base body and the receiving unit for the centrifugal pump means on the second side. The recesses are created by corresponding protrusions in the profile of the first and/or second mold in the injection-molding process.

A mold is to be understood in conjunction with injection-molding methods to be a profiled half-mold whose profile is provided for receiving a polymer melt. The polymer melt flows into the cavity, which results when an additional half-mold is placed on the first half-mold.

A second mold forms a second profile half-mold and has a profile which is complementary in shape to a second side of the base body of the cassette module. The second side is a side which has the receiving unit for the centrifugal pump means. The receiving unit is formed like the fluid channels on the first side by perpendicular wall sections are arranged at right angles on the base plate of the base body. The receiving unit is preferably formed by a cylindrical shape of the wall sections. Accordingly, the second mold has a complementary cylindrical area, which creates the receiving unit by the injection-molding process.

The base body is produced by introducing a polymer melt into the cavity formed by the two mold halves. The polymer melt is distributed in the accessible regions of the cavity, thereby forming the geometry of the base body of a cassette module. The base body in this process is in one piece and contains fluid channels, a receiving unit for the centrifugal pump means and recesses in the base plate, which establish a fluid connection between the fluid channels on the first side of the base body and on the second side of the base body.

After pouring the polymer melt between the half-molds of the casting molds, the polymer melt is cooled to a temperature below its melting point. The term "melting point" in this context is not to be understood strictly as a thermodynamic melting point. In the actual sense, this should be understood to mean that the polymer melt, which has cooled to form the base body, can be removed from the mold without the shape of the base body collapsing during unmolding.

Preferred materials for producing the base body include polypropylenes and copolymers of polypropylene and ethylene. In addition, the polymer melt may also contain thermoplastic elastomer materials, e.g., polymers of styrene block copolymers, e.g., based on styrene, ethylene and butylene repeating units (SEBS) or styrene and isoprene units (SIS). Injection-molded parts produced from these materials can be removed from the mold halves after the process step of cooling and can thus be unmolded.

This method may advantageously be further used to create on the base body a fluid ramp between the receiving unit for a centrifugal pump means and the recess in the base plate to establish a fluid connection between the receiving unit of the second side and a fluid channel on the first side of the base body. The fluid ramp is formed by a bottom, which rises at an inclination in the wall section of the receiving unit, which is arranged in an area at a distance from the base plate to the recess in the base plate in the wall section area of the receiving unit. The profiling of the first and second mold halves is designed to be complementary accordingly.

In particular the use of a cassette module of the type described in the introduction according to any one of Examples 1 to 13 in dialysis is provided. The cassette module, which is especially suitable for this use, is characterized by an arrangement of fluid channels on one side of the base body and the receiving unit for centrifugal pump means on a second side of the base body, as already described in the introduction, such that the fluid channels and the receiving unit are formed by recesses in the base plate of the base body, thus creating fluid connections. In this arrangement, the base body may be manufactured in one piece by the injection-molding method described above. The liquid-carrying components of the cassette therefore need not be assembled from individual parts. The connections of the components to an assembled unit would have to be created by joining methods such as adhesive bonding techniques or welding techniques.

In addition to the increased manufacturing effort, this would also mean an increased risk of damage for the liquids such as blood or dialysis fluids to be processed in the dialysis treatments. First, dead spaces or edge protrusions might then be formed due to the manufacturing process, possibly causing the blood to coagulate or triggering hemolysis. Likewise, a cassette module with an assembled base plate is always at higher risk due to particle contamination than a cassette module manufactured in one piece.

BRIEF DESCRIPTION OF THE FIGURES

FIG. 4 shows a cross-sectional view from a detail of a base body according to FIGS. 2 and 3.

FIG. 5 shows a cross-sectional view of another embodiment of a base body of a cassette module as an alternative to FIGS. 2 and 3.

FIG. 6 shows a detail of a cassette module according to the invention in a perspective of a first side of the cassette module.

DETAILED DESCRIPTION WITH REFERENCE TO THE DRAWING

Figure 1:
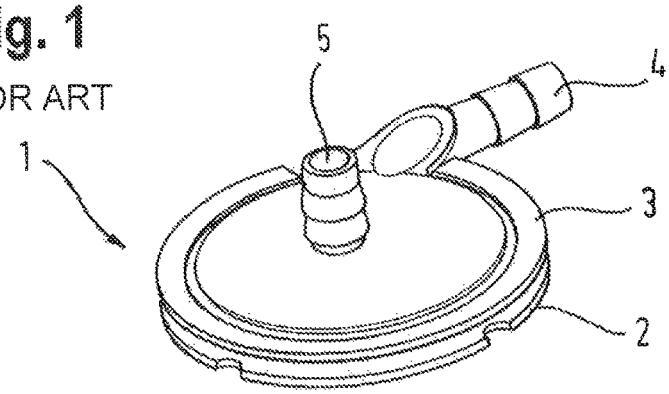
FIG. 1 shows a centrifugal pump known in the state of the art.

FIG. 1 shows a housing of a centrifugal pump 1 as known in the state of the art. The centrifugal pump consists of an upper housing part 3 and a lower housing part 2. An inlet port 5 is mounted at a right angle on the upper housing part 3. An outlet port 4 is mounted tangentially on the lower housing part 2. Inflowing liquid is introduced into the housing 1 through an inlet port 5 along the axis of rotation of the rotor 6 during operation of the pump unit and is discharged again through the outlet port 4. The outlet of the liquid is tangential to the rotor 6 because the speed of the liquid is the greatest there.

Figure 2:
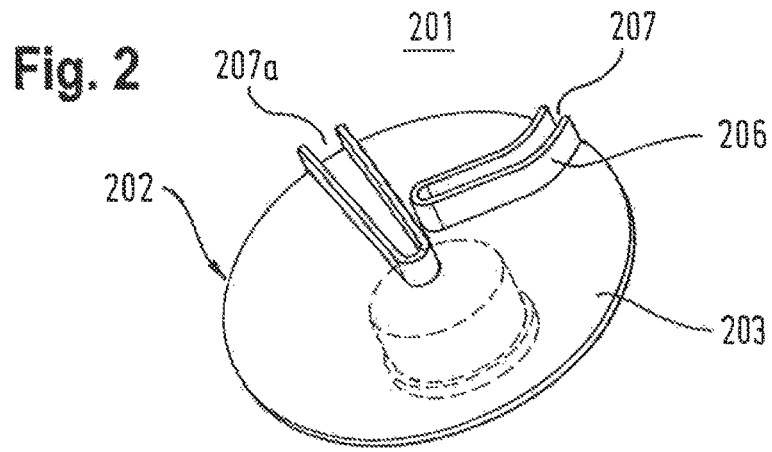
FIG. 2 shows a detail of a base body of a cassette module according to the invention, from a perspective, which makes a first side with fluid channels visible.

FIG. 2 shows a perspective diagram of a detail of a cassette module 201 (not shown in detail) having a base body 202 comprising a base plate 203. This shows a first side of the base body 202 with the arrangement of the fluid channels 207, 207*a*. The fluid channels are formed by vertical side walls 206. The receiving unit for the rotor for conveying liquids on the second side of the base body 202 and of the base plate 203 is concealed in this view.

Figure 3:
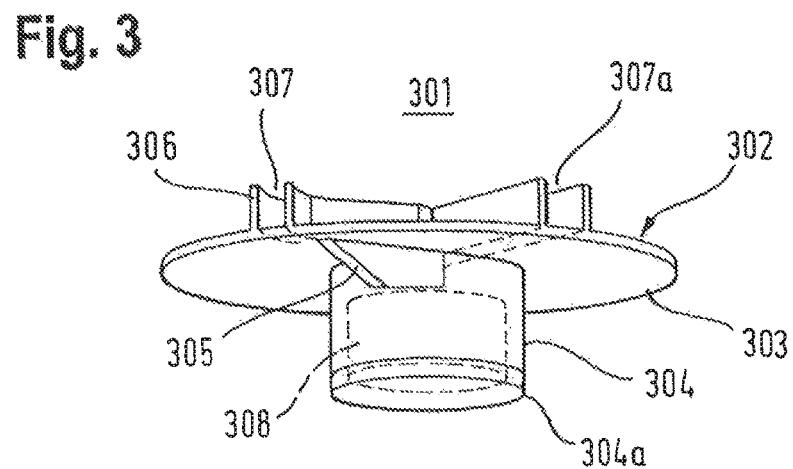
FIG. 3 shows the detail of the base body of a cassette module according to the invention from FIG. 2 from another perspective which makes a second side with a receiving unit for a centrifugal pump means visible.

Figure 3 shows a detail of FIG. 2 in a modified perspective diagram, which shows a detail from the cassette module 301, including a base body 302 with a base plate 303. This diagram shows a second side of the base body 302 with a receiving unit 304 for a rotor as the centrifugal pump means 308 (concealed). The receiving unit 304 consists of cylindrical housing and is in fluid connection with the fluid channels 307, 307*a* formed by vertical side walls 306 on the first side of the base body. The fluid connection of a tangential outlet of the receiving unit 304 is directly adjacent to a fluid ramp 305, so that outflowing fluid is conveyed from the receiving unit on the second side of the base body into the fluid channel 307 on the first side. The centrifugal pump means 308 is still held by a covering cap 304*a* in the receiving unit.

FIG. 4 shows a section through the base body 202 which is perpendicular to the base plate 203 from FIG. 2. This shows the corresponding detail 401 from the cassette consisting of a base body 402 and the base plate 403 of the base body. In general, the base body is understood to be all structurally related details, which contribute to an integral and one-piece design in the diagram. The following are to be understood as integral components of the base body 402, and in general the base body of the other illustrations:
  the receiving unit 404 for the rotor,
  the tangential outlet from the receiving unit 405*a* leading to the fluid ramp (not shown in this figure),
  the vertical side walls 406 which form the fluid channels 407, 407*a*, the base plate 403.

In a sectional diagram the rotor 408, which is held in the receiving unit 404 by the covering cap 404*a*, can be seen in a sectional diagram in the receiving unit. During operation of the pump unit, inflowing fluid is introduced through the incoming channel 407*a* into the receiving unit, accelerated by the impeller 408 and conducted through the outlet into the fluid channel 407.

In an alternative embodiment of FIG. 4, the receiving unit 404 on the base plate is omitted. Accordingly, the cap 404*a* is to be designed, so that the receiving unit is integrated into the cap. In particular, the fluid ramp is then also integrated into the cap.

FIG. 5 shows another embodiment of a detail 501 of a cassette module with the base body 502 and the fluid channels 507, 507*a*. It differs in comparison with FIG. 4 by an altered geometry of the rotor 508, the receiving unit 504 and the covering cap 504*a*. Certain requirements of the power of the pump unit, e.g., the delivery pressure and the flow rate, may necessitate alternative geometries of the rotor. The receiving unit and the covering cap must be adapted geometrically accordingly. In the present case, a rotor whose diameter is larger on the side facing the base plate 503 than on the side facing the covering cap is shown schematically. The receiving unit 504 is adapted to the diameter of the rotor from the geometric dimensions accordingly. The cap 504a is adapted geometrically to the sudden change in the cross-sectional diameter of the rotor.

FIG. 6 shows a perspective view of the detail 601 of a cassette module according to the invention, where the side walls 606 of the fluid channels (concealed) are welded to a covering film 611. The film shows schematically the contours of the welding zones, which correspond to the contours of the vertical side walls 606 of the fluid channels 607 and 607a. The film 611 is permanently attached to the base body 602 via the side walls 606 by the welding, where 609 and 610 denote ports of the fluid channels leading into and out of the pump unit during operation. The film 611 covers multiple fluid channels and even covers the entire detail 601 of the cassette body in the diagram shown here.

Figure 7:
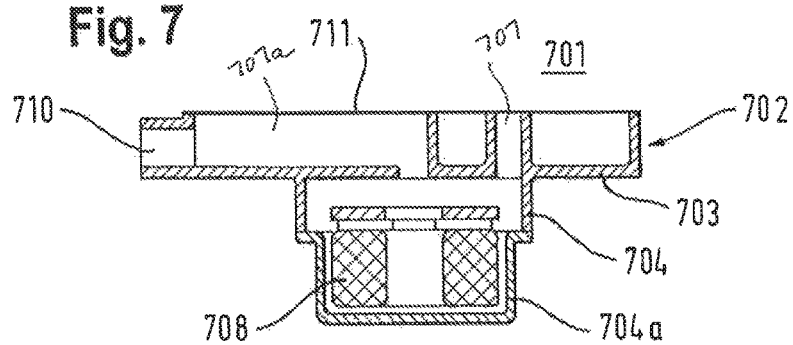
FIG. 7 shows a cross-sectional view of the detail of a cassette module according to FIG. 6.

FIG. 7 shows a cross-sectional view of a detail 701 of a cassette module according to FIG. 6. This figure shows an alternative embodiment of the pump unit consisting of the receiving unit 704, the cap 704a and the rotor 708. Port 710 corresponds to the port 610 of the inlet channel from FIG. 6. Film 711 corresponds to the covering film 611 in FIG. 6. The base body is labeled as 702, the base plate as 703, and the fluid channels as 707a and 707.

Figure 8:
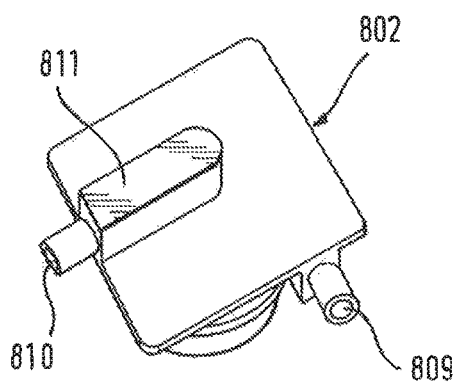
FIG. 8 shows a detail of the base body of an alternative embodiment of a cassette module according to the invention in a perspective which makes the first side visible.

FIG. 8 shows another embodiment of a detail 801 of a cassette module with the direction of view at a first side of the base body 802. Ports 810 and 809 form accesses to the inlet and outlet fluid channels, which are connected to the pump unit. This figure shows an embodiment, in which only the fluid channel of the cassette module shown here is covered with a piece of film 811 and has been welded to the vertical side walls of the fluid channel.

Figure 8A:
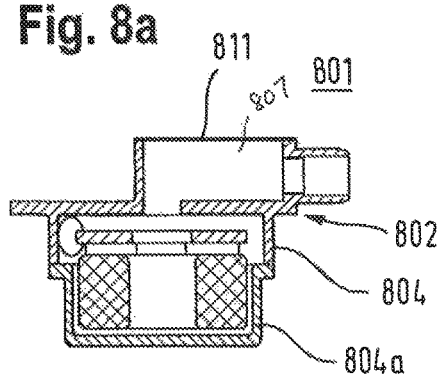
FIG. 8*a* shows a sectional view of a perpendicular section through the detail of the cassette module in FIG. 8.

Figure 8a shows a sectional view of a perpendicular section through the detail of the cassette module in FIG. 8. This figure shows the base body which is integrally connected to the receiving unit 804. This shows that the inlet fluid channel 807 is arranged on the first side of the base body whereas the outlet fluid channel with the outlet port 809 is arranged on the second side of the base body 802. The fluid channels on the first side and the receiving unit and the fluid channels on the second side of the base body still form an integral unit, which can be manufactured in one piece in a one-step injection-molding process. The arrangement of the outlet fluid channel on the second side of the base body may take into account certain requirements in terms of fluidic mechanics. Unlike the embodiments with a fluid ramp, e.g., in FIG. 3, less flow energy of the fluid to be pumped is lost in an embodiment like that shown in FIG. 8a, because it need not be diverted via the inclined ramp to the first side of the base body. In certain applications, the ramp can lower the delivery pressure and the flow rate of the fluid unfavorably. On the other hand, in certain embodiments, it may be advantageous to minimize structures on the second side of the cassette module which are facing the treatment machine during operation and are engaged with this machine. This advantage would be obtained in embodiments according to FIGS. 2 through 7, in which the fluid channels are arranged on the first side of the base body.

Figure 9:
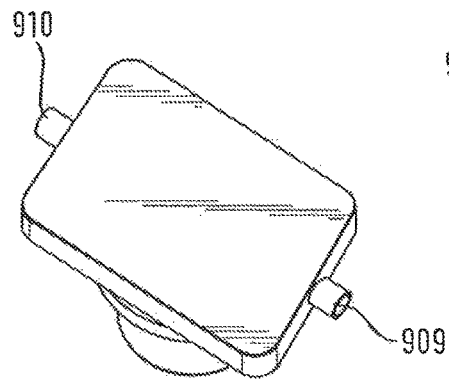
FIG. 9 shows another alternative embodiment of the base body of a cassette module in a perspective which makes a first side of the cassette module visible, on which the fluid channels are covered by a film. In addition, a cross-sectional view of the additional alternative embodiment is also shown.
Figure 9A:
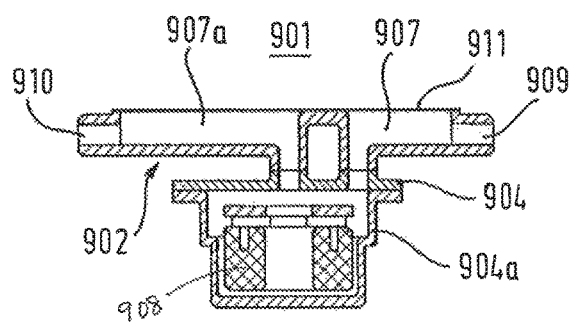
FIG. 9*a* shows a sectional view of a perpendicular section through the detail of the cassette module in FIG. 9.

Figure 9 shows another embodiment of a section 901 of a cassette module, such that as shown in FIG. 9a, the receiving unit for the centrifucal pump means is not integrally connected to the base body 902. The receiving unit is arranged as a coupling plate 904 between the cap 904a and the base body 902 and forms a separate component that can be connected to the base body by welding or adhesive bonding, The rotor 908 is surrounded by the cap 904in the pump housing (formed by the coupling plate 904 and the cap 904a), Inlet and outlet ports and fluid channels 907, 907a, 910 and 909 are integrally connected to the base body. The coupling plate 904 has corresponding passages for the inlet and outlet of fluids to be conveyed. The cap 904amay be equipped with a fluid ramp (not. shown in FIG. 9) as described with regard to the embodiment in FIG. 3. The fluid ramp fulfills the functions of the fluid ramp 305 in FIG. 3.

The fluid channels of the base body are covered by a film 911. This arrangement may be important in particular when the receiving unit must be made of a different material than the base body for certain reasons. For certain embodiments, it may be necessary to eliminate vibrations transmitted to the base plate due to operation of the pump unit. This may be achieved by using a damping material for the coupling plate 904. In general, it is advantageous if the base body is made of a polypropylene copolymer (random PP), a polycarbonate (PC) or a polyethylene terephthalate (PET) in an injection-molding process. The coupling plate 904 may then contain thermoplastic elastomer plastic materials, e.g., SEBS, ethylene-butylene, rubbers or other elastomeric materials, which dampen the mechanical vibrations of the rotor and transmit them to the base plate only in diminished form. This makes it possible to avoid the fact that other function equipment may be sensitive to disturbances due to vibration during operation.

Figure 10:
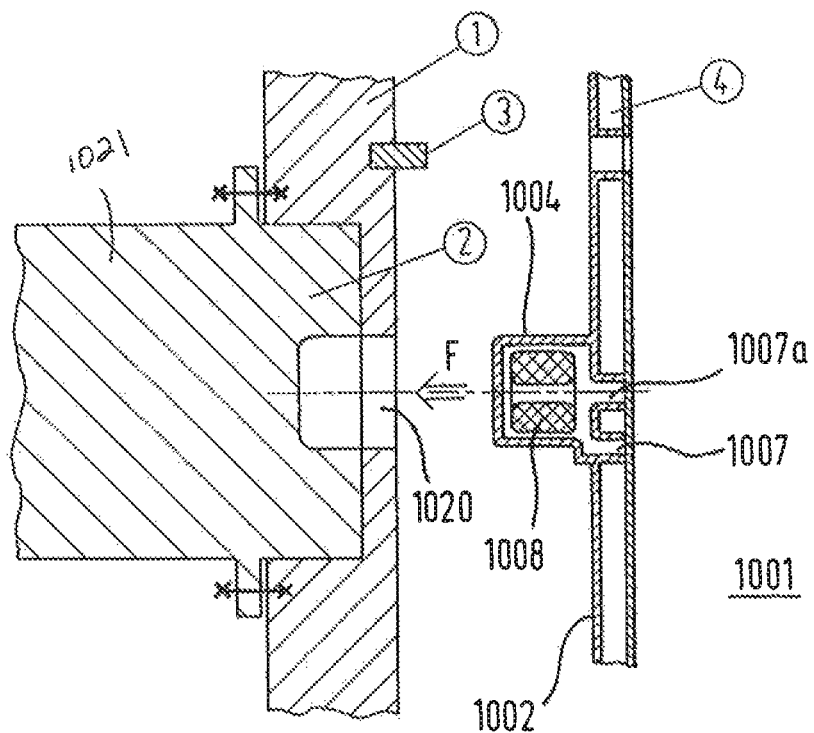
FIG. 10 shows a cross-sectional view of an arrangement of the machine console and a section of a cassette module according to the invention.

FIG. 10 shows a detail 1001 of a cassette module having an integrated rotor 1008 as described in the embodiments of the preceding figures, as well as fluid channels 1007 and 1007a. This figure shows the pump housing 1004, which protrudes beyond the base plate 1002 and may include a receiving unit of the rotor of the embodiments described previously. The pump housing 1004 with the rotor 1008 is designed, so that it can be accommodated by a recess 1020 in the pump drive 1021. The drive generates the magnetic fields, which induce motion of the rotor 1008.

In addition, FIG. 10 shows a molded part 3 on the machine plate, which is part of the machine console that is provided for this purpose and is engaged with the cassette module. The molded part is embodied as a position pin as an example in FIG. 10. Together with the recess 1020 in the rotor drive, the cassette may be arranged so that it is accurately positioned on the machine console and furthermore it can be verified by means of a sensor system (not shown) in the rotor drive unit.

The invention claimed is:

1. An arrangement comprising a cassette module and a machine console of a machine for extracorporeal blood treatment or dialysis, the cassette module including a cassette that has a base body with
    a receiving unit for a magnetic centrifugal pump means on a second side of the base body which is assigned to the machine console in the arrangement,
    fluid channels on a first side of the cassette module which face away from the machine console in the arrangement,
    a molded part on the machine console which is in form-fitting engagement with a complementary molded part on the cassette, and
    an impeller drive which is integrated into the machine console, such that the cassette in the arrangement is in form-fitting and magnetic engagement with the centrifugal pump means of the cassette module.

2. The arrangement according to claim 1, wherein the receiving unit is integrally connected to the base body.

3. The arrangement according to claim 2, wherein the base body together with the receiving unit for the centrifugal pump means and the fluid channels is an injection-molded part.

4. The arrangement according to claim 3, wherein the base body with the fluid channels and the receiving unit for the centrifugal pump means form two separate parts, which are connected to one another.

5. The arrangement according to claim 1, wherein the fluid channels are partially formed by side walls, which are mounted on the base body at a right angle to an extension surface of the base body and border sides of the fluid channels.

6. The arrangement according to claim 1, wherein the receiving unit for the centrifugal pump means on the second side of the base body formed in part by side walls, which are mounted on the base body at a right angle to an extension surface of the base body and border sides of the receiving unit.

7. The arrangement according to claim 1, wherein the fluid channels on the first side or fluid channels on the second side of the base body are covered by a film and together with vertical side walls bordering sides of the fluid channels are at least partially connected and border the fluid channels.

8. The arrangement according to claim 7, wherein multiple fluid channels on one side of the base body are covered by a film and together with the bordering vertical side walls at the sides of the fluid channels are at least partially connected and border the fluid channels.

9. The arrangement according to claim 1, wherein the receiving unit of the centrifugal pump means forms a receiving pot in which a rotor of the centrifugal pump means is accommodated, and vertical side walls are covered with a film and are connected and border the receiving pot.

10. The arrangement according to claim 1, wherein said receiving unit for the centrifugal pump means is in fluid connection with the fluid channels that are arranged on the first side of the base body during operation.

11. The arrangement according to claim 1, wherein said fluid channels arranged on the first side of the base body form inlet and outlet lines for fluid flows to and from the centrifugal pump means.

12. A method of using a cassette module within an arrangement that includes a machine console of a machine for extracorporeal blood treatment or dialysis, the cassette module including a cassette that has a base body with a receiving unit for a magnetic centrifugal pump means on a second side of the base body which is assigned to the machine console in the arrangement, fluid channels on a first side of the cassette module which face away from the machine console in the arrangement, a molded part on the machine console which is in form-fitting engagement with a complementary molded part on the cassette, and an impeller drive which is integrated into the machine console, the method comprising bringing the cassette module into engagement with the machine console, and inserting the magnetic centrifugal pump means into the receiving unit such that the cassette in the arrangement is in form-fitting and magnetic engagement with the centrifugal pump means of the cassette module.

\* \* \* \* \*